(12) United States Patent
Wang et al.

(10) Patent No.: US 10,314,799 B2
(45) Date of Patent: *Jun. 11, 2019

(54) USE OF TAURINE IN PREVENTION AND/OR TREATMENT OF DISEASES INDUCED BY VIRUSES OF GENUS CORONAVIRUS AND/OR GENUS ROTAVIRUS

(71) Applicants: GENIFARM LABORATORIES INC, Guangdong (CN); GUANG ZHOU YUAN TU BIOLOGICAL AND CHEMICAL TECHNOLOGY CO., LTD, Guangdong (CN)

(72) Inventors: Yongdong Wang, Guangdong (CN); Jiyuan Cao, Guangdong (CN); Shifa Zhu, Guangdong (CN); Wen Cheng, Guangdong (CN); Zhipeng Huang, Guangdong (CN)

(73) Assignees: GENIFARM Laboratories Inc, Guangdong (CN); GUANG ZHOU YUAN TU BIOLOGICAL AND CHEMICAL TECHNOLOGY CO. LTD, Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/543,311

(22) PCT Filed: Jan. 17, 2015

(86) PCT No.: PCT/CN2015/070953
§ 371 (c)(1),
(2) Date: Jul. 13, 2017

(87) PCT Pub. No.: WO2016/112552
PCT Pub. Date: Jul. 21, 2016

(65) Prior Publication Data
US 2017/0368006 A1 Dec. 28, 2017

(51) Int. Cl.
*A61P 1/12* (2006.01)
*A61P 31/14* (2006.01)
*A61K 31/185* (2006.01)

(52) U.S. Cl.
CPC .............. *A61K 31/185* (2013.01); *A61P 1/12* (2018.01); *A61P 31/14* (2018.01)

(58) Field of Classification Search
CPC ........... A61P 1/12; A61P 31/14; A61K 31/185
See application file for complete search history.

(56) References Cited

U.S. PATENT DOCUMENTS

2006/0178341 A1* 8/2006 Moon .................. A61K 31/716
514/54
2014/0287065 A1 9/2014 Watson et al.

FOREIGN PATENT DOCUMENTS

| CN | 101869151 | 10/2010 |
| CN | 101966245 | 2/2011 |
| CN | 103127416 | 6/2013 |
| CN | 103230574 | 8/2013 |
| CN | 103341160 | 10/2013 |
| CN | 103417570 | 12/2013 |
| CN | 103006811 | * 2/2014 |
| WO | Wo 2007016123 | * 4/2007 |

OTHER PUBLICATIONS

Canadian Swine Health Board (2013).*
Son et al. (Arch Pharm. Res. 21(5); 531-536).*
Anderson (Doctoral Thesis Swedish Uni. of Agr. Uppsala 2010).*
Kim Youngnanet al, Ribavirin efficiently suppresses porcine nidovirus replication, Virus Research (2013), 171(1), 44-53).
Lee, Jung-Hee, Porcine epidemic diarrhea virus infection:Inhibition by polysaccharide from Ginko biloba exocarp and mode of its action, Virus Research (20158), 195, (148-152).

* cited by examiner

*Primary Examiner* — Shirley V Gembeh
(74) *Attorney, Agent, or Firm* — Defillo & Associates; Evelyn A Defillo

(57) ABSTRACT

The present invention provides use of taurine in prevention and/or treatment of diseases induced by viruses of genus coronavirus and/or genus rotavirus, for example, porcine epidemic diarrhea, porcine transmissible gastroenteritis, rotavirus diarrhea and the like.

6 Claims, No Drawings

USE OF TAURINE IN PREVENTION AND/OR TREATMENT OF DISEASES INDUCED BY VIRUSES OF GENUS CORONAVIRUS AND/OR GENUS ROTAVIRUS

CROSS REFERENCE TO RELATED APPLICATION

This application is a national stage entry of PCT/cn2015/070953 filed Jan. 17, 2015, under the International Convention.

TECHNICAL FIELD OF THE INVENTION

The present invention relates to a technical field of disease prevention and disease treatment, and particularly, relates to new use of a known substance, and more particularly, relates to use of taurine in prevention and/or treatment of diseases induced by viruses of genus coronavirus and/or genus rotavirus.

BACKGROUND OF THE INVENTION

Viruses of genus coronavirus and genus rotavirus may induce various diseases of livestock, and particularly porcine viral diarrhea induced by a porcine transmissible gastroenteritis virus, a porcine epidemic diarrhea virus and/or a porcine rotavirus and the like has become one of the severest diseases threatening pig production.

Until now, there is no effective prevention or treatment method available for the porcine viral diarrhea, for the following reasons:

In one aspect, effective and reliable vaccine has not been successfully developed. In recent years, a separated porcine epidemic diarrhea virus strain has a gene homology of about 86-98% with CV777, which indicates great difficulty in vaccine research and development. In fact, a commercially available PED vaccine or a PED/TGE bivalent vaccine and a PED/TGE/PoRV trivalent vaccine under research and development that have been approved in China, all do not achieve an ideal protection rate on the epidemic diarrhea. The PED vaccine approved for market sale in the United States in 2014 is also subject to such problem. Currently, all around the world, especially in the United States, a feedback technique is widely applied to treat such disease, which is also a helpless choice. First, the feedback needs epidemic materials, that is, materials for the feedback may be obtained only in the case of occurrence of the disease, and once the disease occurs, a great loss may hardly be avoided. Second, an effect of the feedback is not definite, and the disease may recur two or three months later. Third, the feedback may cause biosafety risks, that is, outbreaks of other diseases may be introduced to swine herds, and thus an even greater loss may be caused.

In another aspect, the conventional drugs for prevention or treatment of the diseases do not have a definite effect. For example, none of a interferon, yolk antibody, thymosin peptide and the like achieves an ideal effect on the porcine viral diarrhea. Study made by Kim et al. reveals that the antiviral drug, Ribavirin, is capable of inhibiting replication of PEDV (*Virus Research* (2013), 171(1), 44-53). However, regulations and laws all around the world prohibit using human antiviral drugs for food animals, and use of the antiviral drugs such as Ribavirin, amantadine and the like is prohibited in prevention and treatment of the porcine epidemic diarrhea. Study made by Lee et al. finds that a polysaccharide extracted from a ginkgo testa has inhibition of PEDV in vitro and has an activity superior to that of Ribavirin, as a potential anti-PEDV substance (*Virus Research* (20158), 195, 148-152). However, such study achievement is only limited to experiments in vitro, and the effect in vivo still needs to be proved by using a large number of experiments. Chinese patent applications 2013100930843 and 201310147391.5 disclose treatment and prevention of the porcine epidemic diarrhea by using combined Chinese herbal medicine after being smashed directly. Generally, this treatment or prevention method takes a slower and limited effect, and particularly makes no effect on newborn piglets.

In a further aspect, clinically, a specific dose of a disinfectant such as povidone iodine and the like has ever been orally administered to the diseased piglets for treatment of the epidemic diarrhea, which has a certain effect and improves a survival rate by 5-10%. However, prognosis of the survived suckling piglets is poor, and the piglets grow slowly. Clinically, a supportive therapy is generally employed to help the diseased pigs to resist the disease, i.e. relief of symptoms and correction of dehydration of the diseased pigs are made by using a method of orally feeding water containing oral rehydration salts (ORS) or intraperitoneally supplementing seepage such as glucose electrolyte and the like. This method achieves certain effects on weaned piglets, care pigs and adult pigs, but has a tiny effect on low-day-aged suckling piglets. In US patent application US2014/0287065A1, water containing electrolytes such as sodium hypochlorite, sodium hydroxide and the like is orally administered to pigs to reduce an incidence of dehydration among PEDV-infected grown-up pigs, but the patent fails to provide data convincing the effect on the low-day-aged suckling piglets.

Taurine, also referred to as β-aminoethanesulfonic acid, was originally separated from calculus bovis and named by this. Pure taurine is a colorless or white oblique crystal, and odorless. Taurine has a stable chemical property and is a non-protein amino acid containing sulfur, which is existent in vivo in a free state and is not engaged in biosynthesis of the protein in vivo. As disclosed in the prior arts, taurine can be used for a dietary supplement or a drug. The use of taurine as a drug includes: preventing and treating cardiovascular diseases, exerting a cardiac effect and resisting cardiac arrhythmia, lowering blood fat and cholesterol, lowering blood pressure, lowering blood sugar, strengthening liver and benefiting gallbladder, and effects such as antipyretic effect, analgesic effect, anti-inflammation and the like. Taurine is also commonly used as a pharmaceutical auxiliary material and is added to a drug formulation for strengthening the effect of a major medicine, improving a lack of taurine for patients and enhancing cell protection. Chinese patent 201010505721.X discloses a strengthening effect of taurine on major medicines which are andrographolide and extract of *Hedyotis diffusa*. Chinese patent application 201310072382.4 discloses a synergistic effect of taurine and the major medicine, an interferon, for inhibiting activities of vesicular stomatitis virus as well as murine encephalomyocarditis virus and for a cell protection effect thereof. In addition, it has been formerly reported that a mixture of taurine, compound anthocyanidin and Aspirin can be used for the treatment of porcine reproductive and respiratory syndrome; and *astragalus* and taurine can lower a death rate of BALB/c mice with myocarditis induced by infection of Coxsackievirus B3. However, the prior arts do not report that taurine is used for prevention and/or treatment of diseases induced by viruses of the genus coronavirus, and especially do not report that taurine is used for prevention and treatment of the porcine viral diarrhea.

SUMMARY OF THE INVENTION

To overcome the above deficiencies in the prior art, the present invention provides new medical use of taurine.

In order to achieve the above objective, the present invention is realized by the following technical solution.

The present invention identifies through research that taurine may be used for prevention and/or treatment of a series of diseases induced by viruses of genus coronavirus, for example, porcine epidemic diarrhea and porcine transmissible gastroenteritis, and diseases such as rotavirus diarrhea and the like induced by viruses of genus rotavirus. Because a porcine epidemic diarrhea virus and a porcine transmissible gastroenteritis virus both belong to the viruses of the genus coronavirus, the present invention claims use of taurine in prevention and/or treatment of diseases induced by the coronavirus.

Meanwhile, the present invention claims use of taurine in prevention and/or treatment of porcine viral diarrhea.

The porcine viral diarrhea mainly includes porcine transmissible gastroenteritis (TGE), porcine epidemic diarrhea (PED) and porcine rotavirus (PoRV). In addition, other viruses such as enterovirus infection, porcine adenovirus infection, astrovirus, calicivirus, Norwalk virus, parvovirus, pseudorabies virus and swine fever virus may also cause diarrhea of pigs.

The present invention has found that taurine achieves a more significant effect on prevention and treatment of the porcine epidemic diarrhea than porcine transmissible gastroenteritis and coronavirus diarrhea. Therefore, preferably, the present invention claims use of taurine in prevention and/or treatment of the porcine epidemic diarrhea.

Preferably, the present invention claims use of taurine in prevention and/or treatment of the porcine transmissible gastroenteritis.

Rotavirus gastroenteritis is a disease infecting both human and animals, and is caused by the rotavirus of the genus rotavirus of family reoviridae. Although a death rate caused by this virus is not high, the virus has a great impact on health of human, especially infants, and also exerts a great impact on health and production performance of pigs. Therefore, the present invention claims use of taurine in prevention and/or treatment of diseases induced by viruses of the genus rotavirus. More preferably, the present invention claims use of taurine in prevention and/or treatment of the rotavirus gastroenteritis.

A drug for prevention and/or treatment of diseases induced by viruses of the genus coronavirus, comprises taurine in an effective dose.

A drug for prevention and/or treatment of the porcine viral diarrhea, comprises taurine in an effective dose.

A drug for prevention and/or treatment of the porcine epidemic diarrhea, comprises taurine in an effective dose.

As compared with the prior art, the present invention achieves the following beneficial effects:

The present invention firstly identifies through research that taurine may be used for prevention and/or treatment of a series of diseases induced by viruses of the genus coronavirus and/or the genus rotavirus, for example, the porcine epidemic diarrhea, the porcine transmissible gastroenteritis, the rotavirus diarrhea and the like. This develops a new application field for the medical use of taurine. Meanwhile, the present invention further provides a new effective way for effective prevention and treatment of a series of diseases induced by viruses of the genus coronavirus and the genus rotavirus. Particularly, with respect to the porcine epidemic diarrhea, taurine achieves the most significant treatment effect. With such a highly effective therapeutic drug, a feeding cost and risk of pig production industry may be greatly reduced.

DETAILED DESCRIPTION OF THE PREFERRED EMBODIMENT

The present invention will be further described in detail by specific embodiments. Unless otherwise specified, experiment methods hereinafter are all conventional methods in the art. Unless otherwise specified, the used ingredients or materials are all ingredients or materials that are commercially available. Content described below is preferred implementation of the present invention. It should be noted that for those ordinarily skilled in the art, some improvements may be made without departing from the principles of the present invention and such improvements shall be deemed as falling within the protection scope of the present invention.

Embodiment 1 Use of Taurine in Prevention of Porcine Epidemic Diarrhea of Newborn Piglets Prevention of the porcine epidemic diarrhea on the newborn piglets with taurine was implemented by orally administering taurine to pregnant sows.

Drug administration time: 3-30 days before birth of piglets until 15 days after birth of piglets. In consideration of a use-cost, the drug administration time is preferably 5-20 days before birth of piglets until 10 days after birth of piglets, and more preferably 7-14 days before birth of piglets until 5 days after birth of piglets. The effect is subject to an obvious time-effect relationship. The drug administration time for before birth of piglets directly determines a disease incidence of the newborn piglets.

Drug administration dosage: each pregnant sow was administered with 5-500 g of taurine per day, and the administration was in a single dose or in divided doses. The effect is subject to an obvious quantity-effect relationship.

Specific operations: pregnant sows were selected and excrement thereof was tested by RT-PCR to determine the pregnant sows carrying PEDV in vivo. 60 PEDV-carried pregnant sows were divided into two groups randomly. Control group: conventional feeding; experimental group: conventional feeding+50 g per sow per day of taurine. Prevention results of the two groups are listed in Table 1. As seen from Table 1, the disease incidence and a death rate of the experimental group which was administered with taurine are obviously decreased compared to those of the control group (P<0.01).

TABLE 1

| Group | Dosage of taurine | Disease incidence of the new born piglets (%) | Death rate of the newborn piglets (%) |
|---|---|---|---|
| Control group | 0 | 100% | 96.6% |
| Experimental group | 50 g per sow per day | 85% | 75.1% |

Embodiment 2 Use of Taurine in Treatment of the Porcine Epidemic Diarrhea of Newborn Piglets Treatment of the porcine epidemic diarrhea on newborn piglets with taurine was implemented by orally administering a taurine solution to diseased suckling piglets and administering taurine to lactating sows, that is, simultaneous treatment of both the suckling piglets and the lactating sows.

Drug administration time: the administration by drenching/mixed-feeding was carried out on the day when the disease occurred in the suckling piglets and a non-interrupted administration lasted for 3-10 days. Lactating sows: non-interrupted oral administration lasted for 5-10 days.

Drug administration dosage: the administration by drenching and/or mixed-feeding was carried out on the day when the disease occurred in the suckling piglets. The administration by drenching: 2% taurine solution at a dosage of 1-5 mL per time and it was taken 2-6 times per day. The administration by mixed-feeding: 1-20 g/L of taurine solution was drunk freely. Lactating sows: each sow was administered with 5-500 g of taurine per day and the administration was in a single dose or in divided doses.

Specific operations: 40 litters of diseased newborn suckling piglets and sows thereof were selected and randomly divided into two groups equivalently. Control group: conventional supportive therapy (fluid infusion+antibiotic therapy+atropine sulfate); experimental group: treatment with taurine. Treatment results of the two groups are listed in Table 2. As seen from Table 2, a 10-day-aged survival rate and a weaned survival rate of the piglets in the experimental group are both significantly improved compared to those of the control group (P<0.05), and prognosis of the piglets is good.

TABLE 2

| Group | Dosage of taurine for the lactating sows | Dosage of taurine for the piglets | 10-day-aged survival rate (%) | Weaned survival rate | Prognosis |
|---|---|---|---|---|---|
| Control group | 0 | 0 | 8.3 | 3.2 | Poor |
| Experimental group | 100 g per sow per day | 0.2 g per piglet per day | 22.5 | 20.7 | Good |

Embodiment 3 Use of Taurine in Prevention of the Porcine Epidemic Diarrhea of Weaned Piglets, Care Pigs and Finishing Pigs Prevention of the porcine epidemic diarrhea on the weaned piglets, the care pigs and the finishing pigs with taurine was implemented by orally administering taurine to a swine herd, wherein the administration may be carried out by means of feeding in water or mixed feeding.

Drug administration time: a preventative administration was carried out during an epidemic period of the disease, or in autumn, winter and spring when the temperature was low and changed greatly, that is, in the season when the porcine epidemic diarrhea frequently occurs. Generally, the administration can be carried out for a long-term. In consideration of the use-cost, the drug administration time is preferably 3-30 days, and more preferably, 7-14 days. The effect is subject to an obvious time-effect relationship.

Drug administration dosage: 0.005-2% of taurine was added in daily-drinking water for the pigs to drink freely; or 0.01-5% of taurine was added into the feed, which is equivalent to a dosage of 50-10000 mg per kilogram of body weight per day of taurine, and the administration was in a single dose or in divided doses. The effect is subject to an obvious quantity-effect relationship.

Specific operations: 120 healthy weaned piglets, 120 healthy care pigs and 120 healthy finishing pigs were selected and randomly divided into two groups equivalently. Control group: conventional feeding; experimental group: conventional feeding+taurine (the dosage of taurine was 200 mg per kilogram of body weight per day). The prevention results of the two groups are listed in Table 3. As seen from Table 3, the disease incidence of the experimental group is lowered compared to that of the control group (P<0.05), and the survival rate of the experimental group is higher than that of the control group (P<0.05).

TABLE 3

| Group | | Disease incidence (%) | Survival rate (%) | Prognosis |
|---|---|---|---|---|
| Weaned piglets | Control group | 10 | 91.6 | Normal |
| | Experimental group | 6.6 | 96.6 | Excellent |
| Care pigs | Control group | 8.3 | 95.0 | Normal |
| | Experimental group | 3.3 | 96.6 | Excellent |
| Finishing pigs | Control group | 3.3 | 96.6 | Normal |
| | Experimental group | 0 | 98.3 | Excellent |

Embodiment 4 Use of Taurine in Treatment of the Porcine Epidemic Diarrhea of Weaned Piglets, Care Pigs and Finishing Pigs Treatment of the porcine epidemic diarrhea on the weaned piglets, the care pigs and the finishing pigs with taurine was implemented by orally administering taurine to the pigs, wherein the administration may be carried out by means of feeding in water or mixed feeding.

Drug administration time: the administration was carried out from the day of occurrence of the disease, and in consideration of the use-cost, the drug administration time is preferably 3-30 days, and more preferably 7-14 days. The effect is subject to an obvious time-effect relationship.

Drug administration dosage: 0.1-2% of taurine was added in the daily-drinking water for the pigs to drink freely; or 0.2-5% of taurine was added into the feed, which is equivalent to a dosage of 100-10000 mg per kilogram of body weight per day of taurine, and the administration was in a single dose or in divided doses. The effect is subject to an obvious quantity-effect relationship.

Specific operations: 60 diseased weaned piglets, 60 diseased care pigs and 60 diseased finishing pigs were selected, and were randomly divided into two groups equivalently. Control group: conventional supportive therapy (fluid infusion+antibiotic therapy+atropine sulfate); experimental group: treatment with taurine (the dosage of taurine was 300 mg per kilogram of body weight per day). The treatment results of the two groups are listed in Table 4. As seen from Table 4, the survival rate of the experimental group is higher than that of the control group (P<0.05).

TABLE 4

| Group | | Survival rate (%) | Prognosis |
|---|---|---|---|
| Weaned piglets | Control group | 86.6 | General |
| | Experimental group | 90.0 | Good |
| Care pigs | Control group | 90.0 | General |
| | Experimental group | 93.3 | Good |
| Finishing pigs | Control group | 96.6 | General |
| | Experimental group | 100 | Good |

Embodiment 5

According to methods as described in Embodiment 2 and Embodiment 4, treatment effects of taurine on porcine transmissible gastroenteritis, rotavirus diarrhea and pseudorabies viral diarrhea of the newborn piglets, the weaned piglets, the care pigs and the finishing pigs were tested, as listed in Table 5. The dosage of taurine for the newborn piglets was the same as that in Embodiment 2; and the dosage of taurine for the weaned piglets, the care pigs and the finishing pigs was the same as that in Embodiment 4. As seen from Table 5, taurine can be used for treatment of the porcine transmissible gastroenteritis and the rotavirus diarrhea, but the treatment effects are poorer than the treatment effect of taurine on the porcine epidemic diarrhea. However, taurine has no treatment effect on the pseudorabies viral diarrhea, for following reasons: in one aspect, a pseudorabies virus which belongs to a virus of genus porcine herpesvirus of family herpesviridae, is a virus having relatively strong resistibility among the family herpesviridae and still has infectivity after being treated with 0.5% phenol for 32 days; in another aspect, a category of the virus may be also a factor causing failure of the treatment effect. The porcine pseudorabies virus belongs to a DNA virus, whereas the porcine epidemic diarrhea virus, the porcine transmissible gastroenteritis virus and the rotavirus all belong to RNA viruses.

TABLE 5

| Disease | Age | Group | Survival rate (%) | Prognosis |
| --- | --- | --- | --- | --- |
| Transmissible gastroenteritis | Newborn piglets | Control group | 9.8 | Poor |
| | | Experimental group | 16.6 | Good |
| | Weaned piglets | Control group | 83.3 | Poor |
| | | Experimental group | 90 | Good |
| | Care pigs | Control group | 90 | Poor |
| | | Experimental group | 93.3 | Good |
| | Finishing pigs | Control group | 96.6 | Poor |
| | | Experimental group | 96.6 | Good |
| Rotavirus diarrhea | Newborn piglets | Control group | 88.7 | Poor |
| | | Experimental group | 93.6 | Good |
| | Weaned piglets | Control group | 90 | General |
| | | Experimental group | 96.6 | Good |
| | Care pigs | Control group | 93.3 | General |
| | | Experimental group | 96.6 | Good |
| Pseudorabies viral diarrhea | Newborn piglets | Control group | 0 | — |
| | | Experimental group | 0 | — |
| | Care pigs | Control group | 46.6 | General |
| | | Experimental group | 43.3 | General |

What is claimed is:

1. A method for treating porcine viral diarrhea by orally administering a patient a drug consisting of taurine as an active ingredient, wherein the taurine is administered at 10-20000 mg per kilogram of body weight.

2. The method according to claim 1, wherein the porcine viral diarrhea is a disease induced by viruses of genus coronavirus or genus rotavirus.

3. The method according to claim 2, wherein the disease induced by viruses of the genus coronavirus is porcine epidemic diarrhea or porcine transmissible gastroenteritis.

4. A drug for oral treatment of porcine viral diarrhea, consisting of taurine as an active ingredient, wherein the taurine is administered at 10-20000 mg per kilogram of body weight.

5. The drug according to claim 4, wherein the porcine viral diarrhea is a disease induced by viruses of genus coronavirus or genus rotavirus.

6. The drug according to claim 5, wherein the disease induced by viruses of the genus coronavirus is porcine epidemic diarrhea.

* * * * *